United States Patent
Rubbert et al.

(10) Patent No.: US 6,214,285 B1
(45) Date of Patent: Apr. 10, 2001

(54) PROCESS FOR THERMAL TREATMENT OF A PLASTICALLY MOLDABLE WORKPIECE AND DEVICE FOR SUCH A THERMAL TREATMENT

(75) Inventors: Rudger Rubbert; Friedrich Riemeier, both of Berlin (DE)

(73) Assignee: OraMetrix GmbH, Berlin (DE)

( * ) Notice: Subject to any disclaimer, the term of this patent is extended or adjusted under 35 U.S.C. 154(b) by 0 days.

(21) Appl. No.: 09/324,158

(22) Filed: Jun. 2, 1999

Related U.S. Application Data

(63) Continuation of application No. 08/772,230, filed on Dec. 20, 1996.

(30) Foreign Application Priority Data

Dec. 20, 1995 (DE) .............................................. 195 47 690

(51) Int. Cl.⁷ .................................................. C21D 11/00
(52) U.S. Cl. ............................ 266/87; 266/262; 148/508
(58) Field of Search ....................................... 148/508, 623; 266/249, 262, 274, 78, 87

(56) References Cited

U.S. PATENT DOCUMENTS

| | | |
|---|---|---|
| 2,989,428 | 6/1961 | Wilson . |
| 3,977,915 | 8/1976 | Greenwood . |
| 4,469,530 | 9/1984 | Wyss et al. . |
| 4,757,978 * | 7/1988 | Hodgson et al. ..................... 266/262 |
| 4,758,285 | 7/1988 | Hodgson et al. . |

FOREIGN PATENT DOCUMENTS

| | | |
|---|---|---|
| 1256668 | 9/1965 | (DE) . |
| 3125992 | 1/1983 | (DE) . |
| 195 47 690 | 11/1996 | (DE) . |
| 1498798 | 8/1989 | (RU) . |

OTHER PUBLICATIONS

Patent Application Serial No. 08/772,230, filed Dec. 20, 1996, Entitled: Process for Thermal Treatment of a Plastically Moldable Workpiece and Device for Such a Thermal Treatment, Inventors: Rudger Rubbert and Friedrich Riemeir.

* cited by examiner

*Primary Examiner*—Scott Kastler
(74) *Attorney, Agent, or Firm*—Haynes and Boone LLP

(57) ABSTRACT

A process for heat treatment of a plastically moldable workpiece, by plastically molding the workpiece at a first temperature to form a shape, mechanically restraining the workpiece by means of form-fitting, bringing the workpiece to a second temperature and subjecting it at least partially to a heat treatment, and removing the workpiece, wherein mechanically restraining the workpiece by means of form-fitting is accomplished by embedding the workpiece in a densely packed pourable embedding material located in a container, wherein the embedding material is stressed. The invention also includes an apparatus for practicing the process.

7 Claims, 1 Drawing Sheet

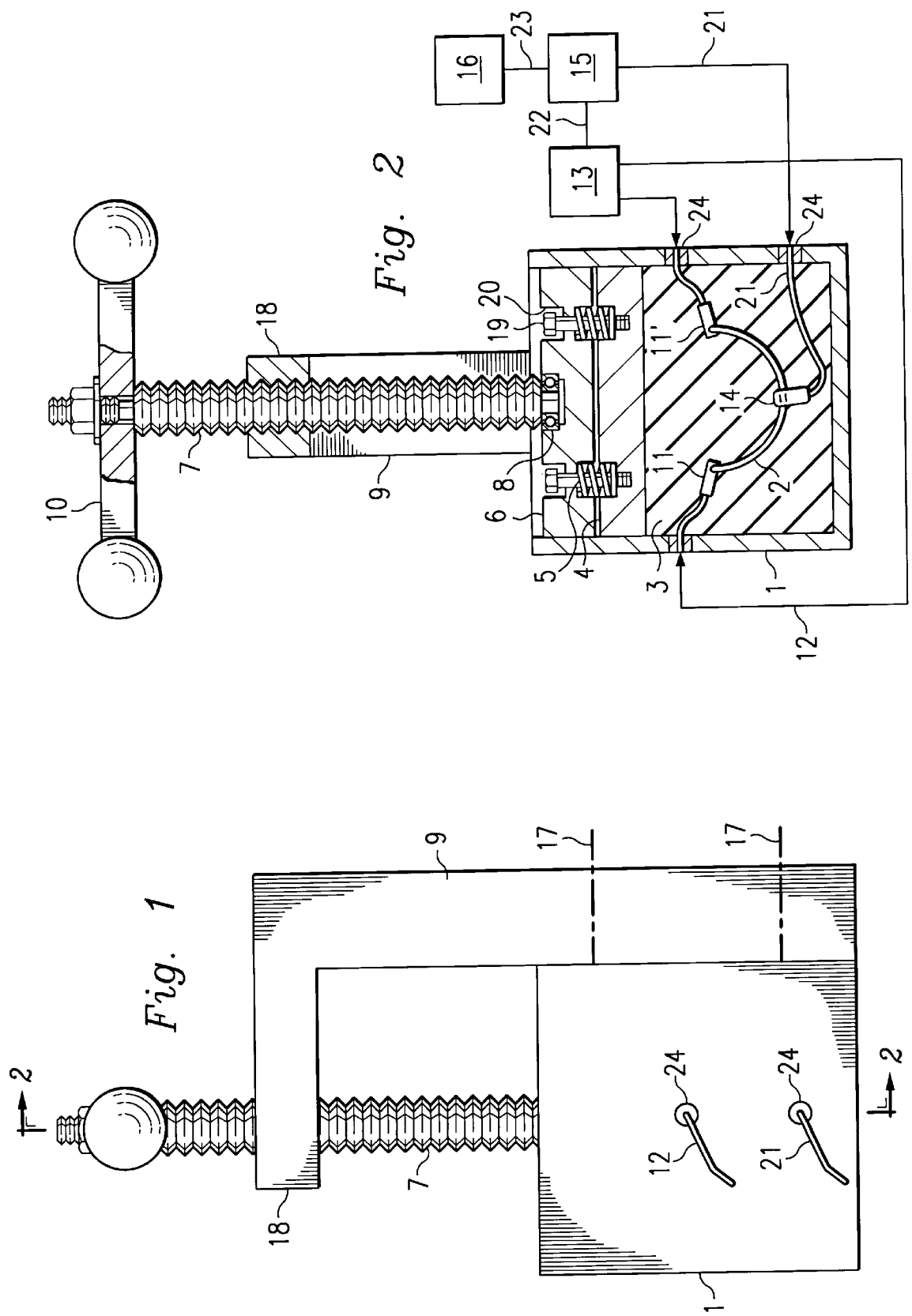

PROCESS FOR THERMAL TREATMENT OF A PLASTICALLY MOLDABLE WORKPIECE AND DEVICE FOR SUCH A THERMAL TREATMENT

This is a continuation of U.S. Ser. No. 08/772,230 filed Dec. 20, 1996 and claims benefit of German Patent Application 19547690.5 filed Dec. 20, 1995.

BACKGROUND OF THE INVENTION

The invention relates to a process for thermal treatment of a plastically moldable workpiece, in which the workpiece is plastically molded at a first temperature, is mechanically restrained in this shape by form-fitting and is brought to a second temperature and at least partially subjected to a thermal treatment, whereafter the workpiece is removed. The invention further relates to a device for such thermal treatment.

Thermal treatment is understood to be a treatment by means of the influence of heat and/or cold, in which a workpiece is subjected to temperatures for a certain length of time in order to influence the properties of said workpiece.

It is known to subject workpieces to heat treatment in order to influence certain properties of the workpiece. Workpieces with a simple configuration are clamped during the heat treatment by devices adapted for form-fitting such that the general shape of the workpiece does not change substantially during the heat treatment. However, the thermally induced changes in volume of the workpiece must not be prevented. The disadvantage of said device adapted for form-fitting is in that the contours of the workpiece must be incorporated in the clamping device. With a complex profile this is sometimes impossible or almost impossible or the costs involved are unreasonably high.

Attempts have already been made to restrain workpieces wherein they are embedded in setting, cross-linking or hardening materials such as, for example, plaster. The removal of the workpiece after heat treatment is very disadvantageous in this case, however, as apart from the considerable soiling caused when plaster is knocked off, there is the danger of distortion and damage to the workpiece. The time required for embedding and removal is also disadvantageous. As a rule new embedding material must be used each time embedding takes place.

Heating also causes difficulties with conventional heat treatment processes and devices, manifest in particular in inexact temperature control. This applies to both heating of the workpiece in a furnace and to resistance heating.

The object of the invention is therefore to provide the process and the device for heat treatment of a plastically moldable workpiece of the type described in the introduction, in order to be able, at a reasonable cost, to continuously surround, in a form-fitting manner, workpieces with a more complex configuration, in particular filigree workpieces, over the whole of their profile or surface, or alternatively over parts of their surface, in order to clamp them.

BRIEF DESCRIPTION OF THE DRAWINGS

FIG. 1 is a view from the side of a heat treatment device according to the invention, shown partially schematically.

FIG. 2 is a sectional view through the device in FIG. 1 along the line A-A'.

BRIEF DESCRIPTION OF THE INVENTION

This object is solved with respect to the process in that, according to the invention, mechanical restraint by means of form-fitting is done by embedding the workpiece in a densely packed pourable embedding material in a container, wherein the embedding material is stressed (i.e., compressed or tensioned). Because of this stressing of a pourable embedding material, in which the workpiece, or at least those parts which have to be restrained by form-fitting, is completely embedded, it is possible for the first time to keep workpieces with an individual and very complex configuration properly mechanically restrained for the desired heat treatment phase. With filigree workpieces, the pourable embedding material conforms very precisely to the respective individual design of surface of the workpiece. In this way, advantageously, any change resulting from the effect of temperature during the thermal treatment is prevented. It is not necessary to construct any special clamping devices which are adapted to an individually designed surface. The embedding material is instead pourable, for example a granular and/or viscous material which can adjust to every individual design of a workpiece surface, without expensive measures having to be undertaken. The pourable embedding material does not need to, and indeed must not set, cross-link or harden, but instead can advantageously be re-used for other shapes after use. The embedding material can be removed very easily from the workpiece. The workpiece has only to be taken hold of and pulled out of the pourable embedding material.

More particularly, the invention includes a process for heat treatment of a plastically moldable workpiece comprising plastically molding the workpiece at a first temperature to form a shape; mechanically restraining the workpiece in the shape by form-fitting; bringing the workpiece to a second temperature to at least partially subject the workpiece to a heat treatment; and removing the workpiece wherein the mechanical restraint by means of form-fitting is done by embedding the workpiece in a densely packed, pourable embedding material located in a container, wherein the embedding material is stressed. The invention also includes an apparatus for practicing the process.

DETAILED DESCRIPTION OF THE INVENTION

It is advantageous according to the invention when the thermal treatment of the workpiece takes place in the pourable embedding material and preferably the temperature or a physical quantity dependent thereon is measured during the change in temperature. The workpiece can be subjected to the thermal treatment desired and the temperature of the workpiece measured while the workpiece is more or less completely surrounded by the embedding material. The embedding material is kept stressed in the container during the thermal treatment. By means of its internal stress it causes the desired resistance against deformation of the workpiece, resulting in perfect mechanical restraint of the workpiece, even when it has an extremely complex profile and external design. The restraint is thus not dependent on the design of the workpiece, so with the new process workpieces of any design can be treated.

When it is described that a thermal treatment takes place in at least a partial manner, this is understood inter alia as a treatment of the workpiece either as a whole or in part. Parts of the workpiece can be subjected to the thermal treatment and not others, and in all cases by means of the measures according to the invention, there is the advantage that during the thermal treatment any distortion of the workpiece is prevented. This applies to all methods of treatment which the skilled person normally employs.

Even when a thermal treatment comprises a cold treatment, for ease of understanding of the invention, a heat treatment is referred to hereinafter.

Advantageously, the temperature of the workpiece is measured with a temperature sensor during the heat treatment. This signal can be fed to a control unit with the aid of which the heat treatment can be controlled precisely, for example by means of at least one control loop by set point/actual value comparison relating to the temperature. Instead of the directly measured temperature, a temperature-dependent electrical parameter of the workpiece can be measured in a direct manner and then lead, in the manner described, to precise control of the temperature for the heat treatment. In this connection, it is conceivable that the temperature regulation is done by means of a microcontroller, which also compares the actual temperature values measured by the sensor with the set point temperature values, and different temperatures and temperature coefficients are preferably selected and regulated at an operator unit. The control unit controls, for example, a current source with the aid of which the workpiece is heated in the desired manner by means of electrical resistance.

With an electrically conductive workpiece which is appropriately contacted and thereby heated, the electric heating of the workpiece preferably takes place in that current is conducted through the workpiece by means of a controllable current source, and heating is by means of electrical resistance.

Instead of the direct temperature measurement, in the case of electric heating of the workpiece, the effective current can be measured by means of the voltage drop in a series resistance. Besides the current, in this case the voltage drop at the workpiece can be measured by means of parallel contacting. The respective resistance is then calculated by a computer from the measured data, and the temperature is calculated from the change in resistance during the application of current to the workpiece over the temperature coefficients of the specific resistance. Again, in this case this information is compared by means of the control unit with the set point temperature value, and the controller controls the current source correspondingly.

It can be advantageous according to the invention to previously provide the control unit with the time characteristic of the desired temperature values as a setpoint curve. It is particularly advantageous according to the invention to use cascaded control loops for current and temperature. It is possible to construct the measuring and evaluating system and the control system using analogue, digital or mixed technologies. It is advantageous according to the invention to use at least one micro-controller for measurement, evaluation and control.

Apart from the heating of the workpiece by radiation, that is to say be means of microwaves or by optical radiation (for example, laser or infra-red light), electric heating of the workpiece by induction also works very well. In the case of convection, hot air can be used advantageously.

According to the invention, different temperature sensors can be used, for example, NTC-PTC resistors and semi-conductors, PT 100 and infra-red sensors.

It is advantageous according to the invention when the size of the particles of the pourable embedding material does not exceed approximately half the mass of the workpiece to be kept mechanically restrained. If, for example, a 1 mm thick flat wire is to be kept exactly planar over a pre-determined distance, for such a workpiece the particle size should not exceed ½ mm. The particle size of the embedding material is advantageously related to the smallest relevant dimension of the workpiece. The keeping of different embedding materials in storage presents no difficulties, wherein the particles of material are classified according to size. It has been shown that the workpieces are optimally stressed with embedding materials having such particle sizes and thereby can be precisely mechanically restrained.

According to the invention powdery or granular materials are envisaged as embedding materials, wherein according to a particularly preferred embodiment according to the invention quartz sand or a mass of spheres is used as the embedding material. It is furthermore possible to manufacture the spheres from glass, ceramics, porcelain or the like. Such an embedding mass is not electrically conductive and can therefore be used for resistance heating and so forth.

The controlled conduction of heat to such a mass of spheres has proved particularly advantageous when during the heat treatment the temperature control is done by means of at least one control loop using the actual value/set point value comparison described above.

A particular embodiment of the invention is characterized in that the thermal treatment takes place by heating and the workpiece is heated in the pourable embedding material by convection or radiation or electrically.

In a further advantageous embodiment of the invention the workpiece is composed of a shape memory alloy and a pre-determined design is programmed into the workpiece by means of the heat treatment. The process according to the invention can be used particularly advantageously in orthodontics. In this case, for example, curved wires are used for corrective re-positioning of teeth, often requiring a large number of bends and torsions specific to the patient to be produced. Substances can be used, inter alia, which require heat treatment or for which it is beneficial. During the heat treatment undesirable re-setting and further distortions can occur. Such distortions can be prevented by means of the process according to the invention. Because of their special properties, with certain substances it is possible to program and, as it were, to imprint the desired, fixed shape into the wires during the heat treatment.

Special substances, for example, super-elastic materials such as nickel-titanium and beta-titanium have a pseudo-ductile substance phase, that is to say permanent cold forming of the workpiece is possible, wherein, however, when heated a capacity for re-setting into the original design of the workpiece, prior to the cold forming, comes into operation. This effect, in which plastically molded workpieces take on their original shape after heating, is also called a "memory effect". If, during the process according to the invention and during the heat treatment the workpieces are held in their new shape, the "memory" re-setting of the workpiece is prevented, and if the material is moreover heated to the temperature required for such a step, the workpiece assumes the new shape, that is to say the capacity for re-setting into the former shape is halted. After cooling, the substance is highly elastic again and when cold formed once more has a "memory capacity" for the shape programmed by the heat treatment.

Because of the wide area of applications using little force resulting from the highly elastic properties, such wire materials are used for corrective re-positioning of teeth. Costs are drastically reduced by means of the process according to the invention compared to conventional processes, and yet a surprisingly large degree of precision can be achieved as the complex wire profile can be completely surrounded and mechanically restrained using the features according to the invention. Regardless of the skill of the operator, for the first time an optimum, and in practice very easily operated, heat treatment is possible, even of filigree workpieces, as they are surrounded and kept stressed in a form-fitting manner over their entire profile or over the surfaces of the sections desired.

The device for thermal treatment of a plastically moldable workpiece of the type described in the introduction is solved according to the invention by means of the features that a container which can be filled with pourable embedding material is provided on at least one side with a plunger movably driven relative to the embedding material, and preferably provided with stopping means. The plunger can be configured in various ways, as long as it is movable only relative to the embedding material for increasing or decreasing the volume of the container. If, for example, the lower part of the container is filled with the pourable embedding material, the workpiece is inserted and afterwards the container is filled with the pourable embedding material until where required the workpiece is completely immersed in the embedding material and is surrounded by it, dense packing of the spheres and stress is produced by driving in the plunger or plungers. Any spaces in the volume of the container without any material are then filled. Following this, the embedding material and the workpiece inserted in it are under stress (compression). If the plunger is kept in this end position, the workpiece remains in this stressed (compressed) and thereby precisely mechanically restrained position during the whole heat treatment. It is advantageous when with a preferred embodiment the diameter of glass beads used as pourable embedding material is less than 500 micrometers. Such embedding materials are also suitable for orthodontics and the example presently described in this connection. Even a filigree design of a curved wire is prevented from changing position and from distortion during heat treatment by the pressurized embedding material. In this way a workpiece can be imprinted with a predetermined design or the design can be memorized in the workpiece.

In a particular embodiment according to the invention the plunger is configured as a pressure plate which is pre-tensioned by means of springs counter to a screw plate and the screw plate can be driven by a screw into a screw nut. Although this is a very simple, but very effective device, it can be very finely adjusted manually or by an electric drive. The values desired are outstandingly reproducible and the temperature can be precisely controlled in accordance with a setpoint curve.

With a further embodiment according to the invention, a temperature sensor can be connected to the workpiece and it can be ensured that the temperature sensor is connected to a control unit.

It is also advantageous when, in accordance with the invention, contact elements and where appropriate a temperature sensor can be connected to the workpiece when the workpiece is electrically conductive, and are connected by means of electric lines to a current source and where appropriate to a control unit. Such a device permits reliable implementation of numerous treatment processes, and the same parameters can be set repeatedly.

Further advantages, features and possibilities for application of the present invention will be seen from the following description of preferred embodiments together with the attached drawings.

A workpiece 2 is accommodated in an embedding material 3 in a box-shaped container 1 such that the container is approximately ⅔ filled. From the open side of the box-shaped pressure-resistant container 1 pressure can be exerted on the embedding material 3 by means of a plunger. In the case of the embodiment described here, this occurs in the following manner.

The container is connected at 17 to a bracket 9 which extends vertically upwards at the side of the container 1, and is horizontally angled in an L-shape in order to form a screw nut 18. Through said nut is guided a screw 7 which is connected at its upper vertical end to a drive element 10 in the form of a cross-bar with spheres connected to the ends. The screw 7 projects from above into the container 1 which is open at the top, downwards into a plunger 6 configured as a screw plate, which is approximately the size of the open side of the container 1. The screw 7 is connected with the screw plate with the aid of thrust bearing 8. This, and thereby the center of pressure of the screw 7, is located in the center of the screw plate 6, so that it can be moved vertically into and out of the interior of the pressure-resistant container 1.

At a distance from the plunger configured as a screw plate 6, there is located a pressure plate 4 of the same size as the screw plate 6. The two plates 4, 6 are connected by means of screws 19 such that the pressure plate 4 can be moved up and down in a vertical direction relative to the screw plate 6. The head of the respective screw 19 is driven against the bottom end of a recess 20 in the screw plate 6 and in this way produces the maximum path of movement of the pressure plate 4 in the direction of the base of the container 1. Each screw 19 is surrounded by a spring 5, which springs are located in recesses, not shown in more detail, in the pressure plate 4 and the screw plate 6. These are pressure springs 5, which keep the pressure plate 4 pre-tensioned downwards towards the embedding material. With respect to the displacement of the pressure plate 4 relative to the screw plate 6, the pressure springs compensate for enlargements in the volume of the items located in the container 1, for example, of the workpiece 2.

In the embodiment shown here, the embedding material 3 is glass beads with a size of less than 500 $\mu$m. The approximately semi-circular workpiece 2 shown is, for example, a curved wire which has to be treated for orthodontic use. The ends of the workpiece 2 are connected with the aid of contact elements 11 and 11' via electric lines 12 to a current source 13. At approximately half-way between the beginning and the end of the long workpiece 2, a temperature sensor 14 is fitted onto the workpiece 2, which is connected via electric lines 21 to a control unit 15 with a microprocessor, for example a micro-controller. This control unit 15 is for its part also connected via a line 22 to the current source 13. Lastly, this control unit 15 is connected via a further line 23 to an operator unit 16.

When a plastically moldable workpiece 2 in the shape of a U-shaped wire is to be subjected to a heat treatment such that the whole workpiece 2 is heated from room temperature to a higher temperature of, for example, 180° C., and afterwards cooled again without the cold impressed filigree design of the workpiece 2 being changed by the heat, the following process is carried out. Prior to the start of the process the screw 7 is located in its upper position so that the container 1 is open at the top and is also accessible from the top. The pressure plate 4 and the plunger plate 6 are located above the container 1 at a distance from its top edge. The base of the container 1 is now covered with a layer of the embedding material 3, that is to say with a layer of glass beads with a diameter of approximately 500 $\mu$m. The 11' and, in the middle between them, to the temperature sensor 14.

The container 1 is then filled with more glass beads until the workpiece 2, the contact elements 11, 11', the temperature sensor 14 and the ends of the cables (for example of the cables 12 and 21) and the cable bushings 24 are covered.

The screw 7 is rotated down by actuation of the drive element 10 such that the pressure plate 4 comes to lie flat on the glass beads 3. In this way the embedding material 3 is surrounded on all sides by the container 1 and the pressure plate 4. Pressure is applied to the embedding material 3 until a pre-determined torque is reached on the drive element 10, so that the glass beads and the embedded workpiece 2 are held so tightly that the workpiece 2 can no longer move.

By actuating an operating element, which is not shown, on the operator unit 16, the control unit 15 is controlled so that the current source allows current to flow through the workpiece 2, for example from the contact element 11' via the contact element 11 through the workpiece 2. In this case the temperature is increased by means of the resistance of the metal workpiece 2. The development of the temperature is sensed by the sensor 14 and can be shown when this is desired. The control unit 15 monitors and controls the flow of current coming from the current source 13 (or which flows back to it) such that the heat treatment is carried out by temperature increase, decrease and where appropriate repeated increase and so forth. An optical or acoustic signal indicates the completion of the heat treatment.

Afterwards, the screw 7 is rotated in the opposite direction, upwards, until the container 1 is again accessible from the top. Now, the glass beads used as the embedding material 3 have only to be poured out, and the workpiece 2 released from the contact elements 11, 11' and the temperature sensor 14, and removed. The next heat treatment can subsequently be carried out in the same or a different manner.

What is claimed is:

1. A system for heat treatment of a plastically moldable electrically conductive workpiece comprising:

a container comprising a bed (for completely embedding the workpiece in) a densely packed pourable electrically nonconductive embedding medium and for mechanically restraining the workpiece molded to a shape at a first temperature;

a current source and electrically conductive contact elements connectable to the molded workpiece for applying an electical current through the workpiece to heat the workpiece to a second temperature to at least partially subject the workpiece to a heat treatment; and a controller connected to the current source for controlling the second temperature by changng the current applied to the conductive contact elements from the current source, the second temperature being precisely controlled in accordance with a control loop for comparing set points to actual values, thereby enabling implementation of numerous treatment processes.

2. The system of claim 1 further comprising:

a plunger provided on at least one side of the container having a drive mechanism for moving the plunger relative to the embedded material to apply pressure to the embedded material, until a selected torque is reached on the drive mechanism so that the embedding medium and the workpiece are held tightly so that the workpiece cannot move.

3. The system of claim 2 wherein the plunger is configured as a pressure plate which is tensioned by springs counter to a screw plate wherein the screw plate can be driven by the drive mechanism having a rotatable screw in a screw nut.

4. The system of claim 1 wherein a temperature sensor is connected to the control unit and to the workpiece.

5. The system of claim 1 further comprising an operator unit connected to the controller for showing the temperature of the workpiece.

6. The system of claim 1 wherein a particle size of the embedding medium does not exceed approximately half the smallest relevant dimension of the workpiece.

7. A system for heat treatment of a plastically moldable electrically conductive workpiece, the workpiece being composed of a shape memory alloy, comprising:

a container comprising a bed for completely embedding the workpiece in a densely packed pourable electrically nonconductive embedding medium and for mechanically restraining the workpiece molded to a shape at a first temperature;

a current source and electrically conductive contact elements connectable to the molded workpiece for applying an electical current through the workpiece to heat the workpiece to a second temperature to at least partially subject the workpiece to a heat treatment; and a controller connected to the current source for controlling the second temperature by changing the current applied to the conductive contact elements from the current source, the second temnperature being precisely controlled in accordance with a control loop for comparing set points to actual values, such that the second temperature is controlled to correspond to a temperature that imprints the restrained shape in the workpiece, thereby enabling implementation of numerous treatment processes.

\* \* \* \* \*